United States Patent
Himmelsbach et al.

(10) Patent No.: US 8,975,277 B2
(45) Date of Patent: *Mar. 10, 2015

(54) 2,3-DIHYDROFURO[2,3-C]PYRIDIN-2-YLPIPERIDINE DERIVATIVES

(71) Applicant: Boehringer Ingelheim International GmbH, Ingelheim am Rhein (DE)

(72) Inventors: Frank Himmelsbach, Mittelbiberach (DE); Elke Langkopf, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 106 days.

This patent is subject to a terminal disclaimer.

(21) Appl. No.: 13/911,138

(22) Filed: Jun. 6, 2013

(65) Prior Publication Data

US 2013/0331410 A1    Dec. 12, 2013

(30) Foreign Application Priority Data

Jun. 12, 2012 (EP) .................................... 12171686

(51) Int. Cl.
| | |
|---|---|
| A01N 43/42 | (2006.01) |
| A61K 31/44 | (2006.01) |
| A01N 43/08 | (2006.01) |
| A61K 31/34 | (2006.01) |
| C07D 471/02 | (2006.01) |
| C07D 307/87 | (2006.01) |
| C07D 307/93 | (2006.01) |
| C07D 491/048 | (2006.01) |
| C07D 491/04 | (2006.01) |

(52) U.S. Cl.
CPC .......... *C07D 491/048* (2013.01); *C07D 491/04* (2013.01)
USPC ............ 514/302; 514/469; 546/115; 549/462

(58) Field of Classification Search
None
See application file for complete search history.

(56) References Cited

FOREIGN PATENT DOCUMENTS

| WO | 2007003961 A2 | 1/2007 |
|---|---|---|
| WO | 2011138427 A2 | 11/2011 |
| WO | 2011140161 A1 | 11/2011 |
| WO | 2012080476 A1 | 6/2012 |

OTHER PUBLICATIONS

International Search Report and Written Opinion, Form PCT/ISA/220, for PCT/EP2013/061653, mailed Jul. 4, 2013.
Fyfe, et al. "GPR119 agonists as potential new oral agents for the treatment of type 2 diabetes and obesity" Expert Opinon on Drug Discovery, Informa Healthcare, vol. 3, No. 4, 2008, p. 403-413.
Jones, et al., "GPR119 agonists for the treatment of type 2 diabetes", Therapeutic Patents, vol. 19, No. 10, 2009, p. 1339-1359.
Jones. et al., "The Emergence of GPR119 Agonists as Anti-Diabetic Agents" Annual Reports in Medicinal Chemistry, vol. 44, 2009, p. 149-170.
Wu, et al., "2,5-Disubstituted pyridines as potent GPR119 agonists", Bioorganic and Medicinal Chemistry Letters, vol. 20, No. 8, 2010, p. 2577-2581.

*Primary Examiner* — Jeffrey S. Lundgren
*Assistant Examiner* — Michael Schmitt
(74) *Attorney, Agent, or Firm* — Michael P. Morris; Timothy X. Witkowski

(57) ABSTRACT

The present invention relates to compounds of general formula I,

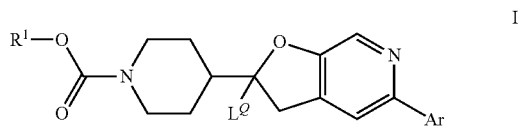

wherein the groups $R^1$, $L^Q$ and Ar are as defined in the application, which have valuable pharmacological properties, and in particular bind to the GPR119 receptor and modulate its activity.

9 Claims, No Drawings

2,3-DIHYDROFURO[2,3-C]PYRIDIN-2-YLPIPERIDINE DERIVATIVES

FIELD OF THE INVENTION

The present invention relates to new compounds, in particular compounds of the formula I

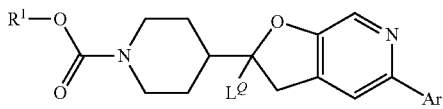

wherein the groups $R^1$, $L^Q$ and Ar are defined as hereinafter, to processes for preparing such compounds, to their use as modulators of the G-protein-coupled receptor GPR119, to methods for their therapeutic use, in particular in treating diseases and conditions mediated by the modulation of the G-protein-coupled receptor GPR119, and to pharmaceutical compositions comprising them.

BACKGROUND OF THE INVENTION

Diabetes mellitus is a serious metabolic disease which affects more than 100 million people worldwide. In the USA there are more than 12 million diabetics with 600,000 new cases diagnosed every year. The prevalence of diabetes mellitus is increasing, which means in particular a high frequency of complications as well, leading to a substantial impairment of quality of life and life expectancy. Because of diabetes-associated microvascular complications, in the industrialised countries type 2 diabetes is currently the most common cause of adult-onset loss of vision, renal insufficiency and amputations. In addition, type 2 diabetes is associated with a two- to five-fold increase in the risk of cardiovascular disease.

The UKPDS study (United Kingdom Prospective Diabetes Study) showed that intensive treatment with common therapeutic agents, e.g. metformin, sulphonylureas or insulin, results in only a limited improvement in glycaemic control (difference in the HbA1c value ~0.9%). Moreover, glycaemic control deteriorated considerably over time even in patients in the intensive treatment group, and this was put down to a deterioration in beta cell function. Diabetes is also a major cause of damage to the retina at the back of the eye and increases the risk of cataract and glaucoma. Finally, diabetes is associated with nerve damage, particularly in the legs and feet, which affects the patient's ability to feel pain and contributes to serious infections. All in all, complications of diabetes are one of the major causes of death worldwide.

Adiposity (obesity) is the result of an imbalance between calorie intake and energy consumption. It correlates to a high degree with insulin resistance and diabetes. However, the molecular mechanisms that are involved in obesity/diabetes syndromes are not yet clear. At an early stage of the development of obesity, an increased insulin secretion balances out the insulin resistance and protects the patient from hyperglycaemia. However, after a time, the beta cell function worsens and non-insulin-dependent diabetes develops in about 20% of the obese population. Obesity has thus become a critical risk factor for diabetes, but the factors that predispose one group of patients to a pathological change in insulin secretion as a response to the accumulation of fat are currently unknown. Obesity also significantly increases the risk of the development of cardiovascular disease. Diabetes is also implicated in the formation of kidney complaints, eye complaints and problems of the nervous system. Kidney disease, also known as nephropathy, sets in when the filtering mechanism of the kidneys is disrupted and proteins escape into the urine in excessive amounts and finally the kidney fails. Therefore there is a medical need for medicaments for preventing and/or treating metabolic disorders (particularly diabetes, predominantly type 2 diabetes) and the complications thereof. In particular there is a need for medicaments with good activity in terms of glycaemic control, disease-modifying properties and reducing cardiovascular morbidity and mortality, and which also have a better safety profile.

Dyslipidemia is a disorder of lipoprotein metabolism, including lipoprotein overproduction or deficiency. Dyslipidemias may be manifested by elevation of the total cholesterol, LDL cholesterol and triglyceride and free fatty acid concentrations, and a decrease in high-density lipoprotein (HDL) cholesterol concentration in the blood. Dyslipidemia occurs often in situations including diabetes, a common cause of lipidemia. For adults with diabetes, it has been recommended that the levels of LDL, HDL, and total cholesterol, and triglyceride be measured every year. Optimal LDL cholesterol levels for adults with diabetes are less than 100 mg/dL (2.60 mmol/L), optimal HDL cholesterol levels are equal to or greater than 40 mg/dL (1.02 mmol/L), and desirable triglyceride levels are less than 150 mg/dL (1.7 mmol/L).

GPR119 is a G-protein coupled receptor (also known as GPCR2, RUP3, SNORF25 or GDIR) which is expressed predominantly in the beta cells of the pancreas and in the K- and L-cells of the intestine. The GPR119 receptor and isoforms have been identified in mammalian species including human, rat, mouse, hamster, chimpanzee, rhesus monkey, cattle and dog. The expression of GPR119 in the pancreas and particularly in the pancreatic β-cells led to the hypothesis that the GPR119 receptor could have effects upon insulin secretion. Activation of the receptor stimulates the cAMP signal pathway, increasing the intracellular levels of cAMP in these cells. This will lead to an improved diabetic situation by a dual action of such a compound: stimulation of cAMP in the beta cell occurs directly via activation of GPR119 in these cells and furthermore indirectly via stimulation of the release of neuroendocrine peptides like GIP and GLP-1 and PYY from the gut. The release of these peptides may have also additional beneficial effects, e.g. on food intake, gastric emptying and other yet unknown functions. Also, a GPR119 agonist can be expected to bring about an improvement in the beta cell function and the beta cell mass. In fact, activation of GPR119 stimulates insulin secretion in-vitro and in-vivo (in rodents) in a glucose-dependent manner. The discovery of two endogenous ligands, lysophospha-tidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm. 2005, 744-751; Cell Metabolism 2006, 167-175; Endocrinolgy 2007, 2601-9). It has recently been shown that GPR119 agonists effectively lower the blood glucose levels in diabetic rodents without the risk of hypoglycaemia. GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Therefore the GPR119 agonists may be expected to have a therapeutic benefit in metabolic diseases. Examples of such diseases include type 1 diabetes, type 2 diabetes, insufficient glucose tolerance, insulin resistance, hyper-glycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction and bone-related diseases (such as osteoporosis, rheumatoid arthritis or osteoarthritis). For comparison and additional information also see 1. Dhayal, S., Morgan, N. G. The significance of GPR119 agonists as a future treatment for type 2 diabetes. Drug News Perspect. 2010, 23(7), 418-24.
2. Yoshida, S., Tanaka, H., Oshima, H., Yamazaki, T., Yonetoku, Y., Ohishi, T., Matsui, T., Shibasaki, M. AS1907417, a novel GPR119 agonist, as an insulinotropic and β-cell preservative agent for the treatment of type 2 diabetes. Biochem Biophys Res Commun. 2010, 400(4), 745-51.
3. Jones, R. M., Leonard, J. N., Buzard, D. J., Lehman, J. GPR119 agonists for the treatment of type 2 diabetes. Expert Opinion on Therapeutic Patents 2009, Vol. 19, No. 10: 1339-1359.

Aim of the Present Invention

The aim of the present invention is to provide new compounds, in particular new 2,3-dihydro-furo[2,3-c]pyridin-2-yl-piperidine derivatives, which are active with regard to the G-protein-coupled receptor GPR119.

Another aim of the present invention is to provide new compounds, in particular new 2,3-dihydro-furo[2,3-c]pyridin-2-yl-piperidine derivatives, which are agonists of the G-protein-coupled receptor GPR119.

A further aim of the present invention is to provide new compounds, in particular new 2,3-dihydro-furo[2,3-c]pyridin-2-yl-piperidine derivatives, which have an activating effect on the G-protein-coupled receptor GPR119 in vitro and/or in vivo and possess suitable pharmacological and pharmacokinetic properties to use them as medicaments.

A further aim of the present invention is to provide effective GPR119 agonists, in particular for the treatment of metabolic disorders, for example diabetes, dyslipidemia and/or obesity.

A further aim of the present invention is to provide methods for treating a disease or condition mediated by the activation the G-protein-coupled receptor GPR119 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular 2,3-dihydro-furo[2,3-c]pyridin-2-yl-piperidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

It has now been found that the compounds according to the invention described in more detail hereinafter have surprising and particularly advantageous properties, and in particular as GPR119 agonists.

In a first aspect the invention thus relates to a compound of formula I wherein

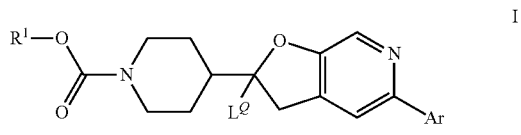

$R^1$ is selected from the group $R^1$-G1 consisting of $C_{1-4}$-alkyl, in which at least one hydrogen atom is replaced by F;

Ar is selected from the group Ar-G1 consisting of

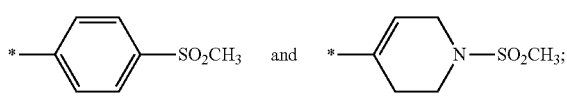 [SMILES: *c1ccc(S(C)(=O)=O)cc1 ; "and" ; *C1=CCN(S(C)(=O)=O)CC1]

and $L^Q$ is selected from the group $L^Q$-G1 consisting of H and $C_{1-3}$-alkyl;

including any tautomers and stereoisomers thereof, or a salt thereof, or a solvate or hydrate thereof.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR119 in a patient in need thereof characterized in that a compound of general formula I or a pharmaceutically acceptable salt thereof is administered to the patient.

According to another aspect of the invention, there is provided a method for treating a metabolic disease or disorder in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR119 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to a use of a compound of the general formula I or a pharmaceutically acceptable salt thereof in combination with one or more additional therapeutic agents for the treatment of diseases or conditions which are mediated by the activation of the G-protein-coupled receptor GPR119.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly Ar, $R^1$ and $L^Q$, are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:
$R^1$-G1:

The group $R^1$ is preferably selected from the group $R^1$-G1 as defined hereinbefore and hereinafter.

$R^1$-G2:

According to one embodiment the group $R^1$ is selected from the group $R^1$-G2 consisting of —CH(CH$_3$)(CF$_3$).

Ar:
Ar-G1:

The group Ar is preferably selected from the group Ar-G1 as defined hereinbefore and hereinafter.

Ar-G2:

In one embodiment the group Ar is selected from the group Ar-G2 consisting of

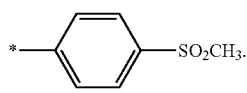

Ar-G3:

In one embodiment the group Ar is selected from the group Ar-G3 consisting of

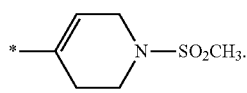

$L^Q$:
$L^Q$-G1:

The group $L^Q$ is preferably selected from the group $L^4$-G1 as defined hereinbefore and hereinafter.

$L^Q$-G2:

In another embodiment the group $L^Q$ is selected from the group $L^4$-G2 consisting of H and methyl.

$L^Q$-G3:

In another embodiment the group $L^Q$ is selected from the group $L^4$-G3 consisting of H.

$L^Q$-G4:

In another embodiment the group $L^Q$ is selected from the group $L^4$-G4 consisting of methyl.

The following preferred embodiments of compounds of the formula I are described using generic formulas (I.1) to (I.5), wherein any tautomers and stereoisomers, solvates, hydrates and salts thereof, in particular the pharmaceutically acceptable salts thereof, are encompassed.

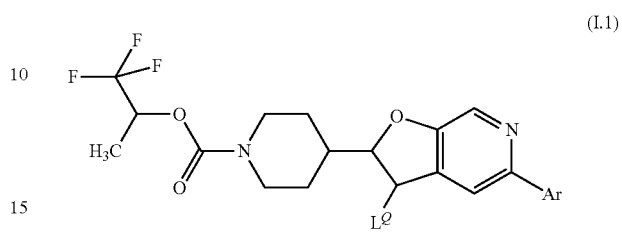
(I.1)

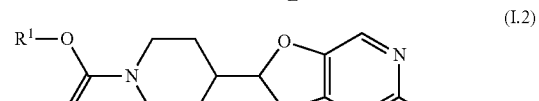
(I.2)

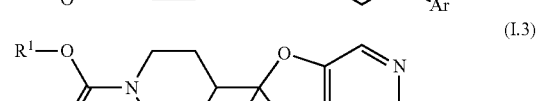
(I.3)

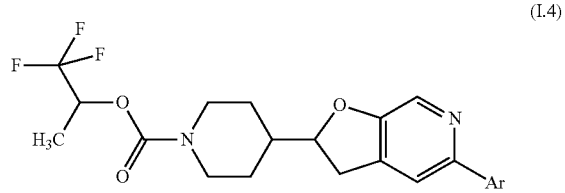
(I.4)

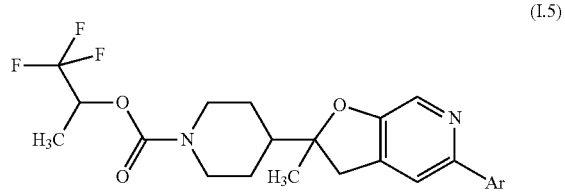
(I.5)

wherein in each of the above formulas (I.1) to (I.5), the groups $R^1$, $L^Q$ and Ar are defined as hereinbefore and hereinafter.

Further preferred embodiments of compounds of the formula I are described by generic formulas (I.R) and (I.S), wherein any tautomers and stereoisomers, solvates, hydrates and salts thereof, in particular the pharmaceutically acceptable salts thereof, are encompassed.

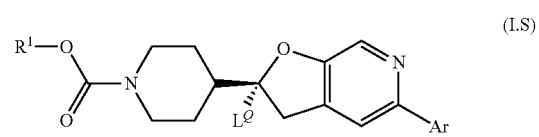
(I.S)

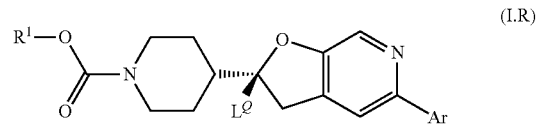
(I.R)

wherein in each of the above formulas (I.R) and (I.S), the groups $R^1$, $L^Q$ and Ar are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | Formula | R$^1$- | Ar- | L$^Q$- |
|---|---|---|---|---|
| E-1 | I | R$^1$-G1 | Ar-G1 | L$^Q$-G1 |
| E-2 | I | R$^1$-G2 | Ar-G2 | L$^Q$-G2 |
| E-3 | I | R$^1$-G2 | Ar-G3 | L$^Q$-G2 |
| E-4 | I | R$^1$-G2 | Ar-G1 | L$^Q$-G3 |
| E-5 | I | R$^1$-G2 | Ar-G1 | L$^Q$-G4 |
| E-6 | I.R | R$^1$-G1 | Ar-G1 | L$^Q$-G1 |
| E-7 | I.R | R$^1$-G2 | Ar-G2 | L$^Q$-G2 |
| E-8 | I.R | R$^1$-G2 | Ar-G3 | L$^Q$-G2 |
| E-9 | I.R | R$^1$-G2 | Ar-G1 | L$^Q$-G3 |
| E-10 | I.R | R$^1$-G2 | Ar-G1 | L$^Q$-G4 |
| E-11 | I.S | R$^1$-G1 | Ar-G1 | L$^Q$-G1 |
| E-12 | I.S | R$^1$-G2 | Ar-G2 | L$^Q$-G2 |
| E-13 | I.S | R$^1$-G2 | Ar-G3 | L$^Q$-G2 |
| E-14 | I.S | R$^1$-G2 | Ar-G1 | L$^Q$-G3 |
| E-15 | I.S | R$^1$-G2 | Ar-G1 | L$^Q$-G4 |
| E-16 | I.1 | — | Ar-G1 | L$^Q$-G1 |
| E-17 | I.1 | — | Ar-G1 | L$^Q$-G2 |
| E-18 | I.1 | — | Ar-G1 | L$^Q$-G3 |
| E-19 | I.1 | — | Ar-G1 | L$^Q$-G4 |
| E-20 | I.1 | — | Ar-G2 | L$^Q$-G2 |
| E-21 | I.1 | — | Ar-G3 | L$^Q$-G2 |
| E-22 | I.2 | R$^1$-G1 | Ar-G1 | — |
| E-23 | I.2 | R$^1$-G2 | Ar-G1 | — |
| E-24 | I.2 | R$^1$-G1 | Ar-G2 | — |
| E-25 | I.2 | R$^1$-G1 | Ar-G3 | — |
| E-26 | I.3 | R$^1$-G1 | Ar-G1 | — |
| E-27 | I.3 | R$^1$-G2 | Ar-G1 | — |
| E-28 | I.3 | R$^1$-G1 | Ar-G2 | — |
| E-29 | I.3 | R$^1$-G1 | Ar-G3 | — |
| E-30 | I.4 | — | Ar-G1 | — |
| E-31 | I.5 | — | Ar-G1 | — |

Particularly preferred compounds, including their tautomers and stereoisomers, the salts thereof, or any solvates or hydrates thereof, are described in the experimental section hereinafter.

Preferred Compounds According to the Invention are:
(a) 4-[5-(4-Methanesulfonyl-phenyl)-2,3-dihydro-furo[2,3-c]pyridin-2-yl]-piperidine-1-carboxylic acid 2,2,2-trifluoro-1-methyl-ethyl ester,
(b) 4-[5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester,
(c) 4-[5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester, and
(d) 4-[5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester;
including any tautomers and stereoisomers thereof, or a salt, solvate or hydrate thereof.

The following compounds are mentioned as examples of compounds according to the invention:
(1) (S)-4-[(R)-5-(4-Methanesulfonyl-phenyl)-2,3-dihydro-furo[2,3-c]pyridin-2-yl]-piperidine-1-carboxylic acid 2,2,2-trifluoro-1-methyl-ethyl ester,
(2) (R)-4-[(R)-5-(4-Methanesulfonyl-phenyl)-2,3-dihydro-furo[2,3-c]pyridin-2-yl]-piperidine-1-carboxylic acid 2,2,2-trifluoro-1-methyl-ethyl ester,
(3) (R)-4-[(R)-5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester,
(4) (S)-4-[(R)-5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester,
(5) (S)-4-[(S)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester,
(6) (R)-4-[(R)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester,
(7) (S)-4-[(R)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester,
(8) (R)-4-[(R)-5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester, and
(9) (S)-4-[(R)-5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester, including any tautomers and stereoisomers thereof, or a salt thereof or a solvate or hydrate thereof.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I', L$^Q$ is H, are accessible using the synthetic route sketched in Scheme 1; R$^1$ and Ar have the meanings as defined hereinbefore and hereinafter. Starting with compound 1 the target compounds are obtained upon partial reduction of the furo[2,3-c]pyridine. The reaction is preferably conducted with hydrogen as the reducing agent in the presence of a transition metal catalyst. Suited transition metals may be derived from Ni, Pd, Pt, Ir, and Rh, such as Raney nickel, Pd on carbon, Pt on carbon, Rh on carbon, PtO$_2$, and Rh$_2$O$_3$. The reduction is preferably carried out in tetrahydrofuran, acetone, ethyl acetate, alcohol, e.g. methanol, ethanol, or isopropanol, acetic acid, or mixtures thereof, at hydrogen pressures of 1 to 100 bar, at 0 to 120° C. Alternatively, formic acid or a formate instead of hydrogen may be used as reducing agent.

The reduction may also be accomplished with a silane or sodium amalgam as reducing agent. Reduction using a silane is for example conducted with triethylsilane and trifluoroacetic acid in dichloromethane, chloroform, acetonitrile, mixtures thereof, or without a solvent in trifluoroacetic acid, at −20 to 120° C. Sodium amalgam is frequently employed in an aqueous solution with sodium hydroxide or sodium bicarbonate.

Scheme 1

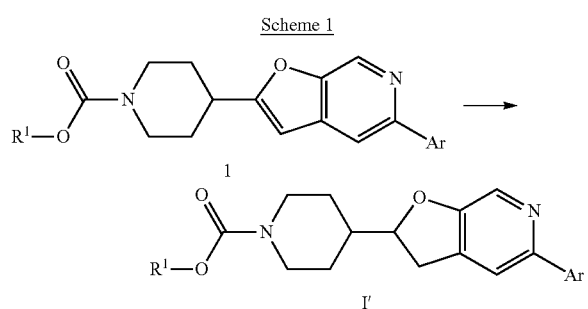

Compound 1, in turn, may be obtained from compound 4, bearing two replaceable halogen or pseudo-halogen groups, as described in Scheme 2; $R^1$ and Ar have the meanings as defined hereinbefore and hereinafter. Depending on the reactivity of the two carbon atoms bearing the halogen or pseudo-halogen groups, the two coupling partners, 6 and 5, are introduced following the sequence depicted on the top or bottom of the scheme. Both residues are preferably attached via a transition metal catalyzed reaction, preferably mediated by a palladium, nickel, copper, or iron species. The active catalyst may be a complex of the transition metal with ligands such as phosphines, e.g. tri-tert-butylphosphine, tricyclohexyl-phosphine, optionally substituted biphenyl-dicyclohexyl-phosphines, optionally substituted biphenyl-di-tert-butyl-phosphines, 1,1'-bis(diphenylphosphino)-ferrocene, triphenylphosphine, tritolylphosphine, or trifurylphosphine, phosphites, 1,3-disubstituted imdiazole carbenes, 1,3-disubstituted imidazolidine carbenes, dibenzylideneacetone, allyl, or nitriles, an elemental form of the transition metal, such as palladium on carbon or nanoparticles of iron or palladium, or a salt, such as fluoride, chloride, bromide, acetate, triflate, or trifluoroacetate. Ar-M is preferably a boronic acid, trifluoroborate, boronic ester, zinc halide, or magnesium halide of Ar and alkyne 5 is preferably used as is or zinc acetylide. Depending on the nucleophiles the reactions are preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, at −10 to 160° C. Additives such as halide salts, e.g. lithium chloride, potassium fluoride, tetrabutylammonium fluoride, hydroxide sources, such as potassium hydroxide or potassium carbonate, amines, such as triethylamine, diisopropylamine, and ethyldiisopropylamine, silver salts, such as silver oxide or triflate, and/or copper salts, such as copper chloride or copper thiophene-2-carboxylate, may be beneficial or even essential for the reaction to proceed. The conditions for the coupling of alkyne 5 with one of the electrophiles, 2 or 4, may bring about the subsequent cyclization as well and thus provide the furo[2,3-c]pyridine. For instance, with $Pd(PPh_3)_2Cl_2$, CuI, and triethylamine in N,N-dimethylformamide at 20 to 140° C. the furo[2,3-c]pyridine may be obtained directly. If the intermediate alkyne is obtained the furo[2,3-c]pyridine may be formed in a separate step using, for example, $Bu_4NF$ in tetrahydrofuran at 50 to 70° C., NaOH in aqueous solution at elevated temperature, CuI or CuCN, optionally in the presence of $NEt_3$, in N,N-dimethylformamide at elevated temperature, $AuCl(PPh_3)$ and $AgOSO_2CF_3$ in $CH_2Cl_2$ or tetrahydrofuran, $AgOSO_2CF_3$, optionally in the presence of trifluoroacetic acid, in $CH_2Cl_2$, Pd, e.g. $PdCl_2$, or other transition metals such as Rh. The furo[2,3-c]pyridine may also be assembled from a constellation in which the oxygen to cyclize (oxygen at the carbon atom next to the carbon atom bearing the alkynyl group) is embedded in an amide group of an aza-heterocyclic group provided the additional group on the amide N is cleavable under the reaction conditions (see e.g. *Synthesis* 2007, 3117). The reactivities of the reaction partners (reacting carbons) described may be reversed, i.e. compounds 2, 3, and 4 are the nucleophile bearing M and compounds 5 and 6 are the electrophile bearing $Hal^1$ or $Hal^2$, providing the same products under the same or similar conditions.

Scheme 2

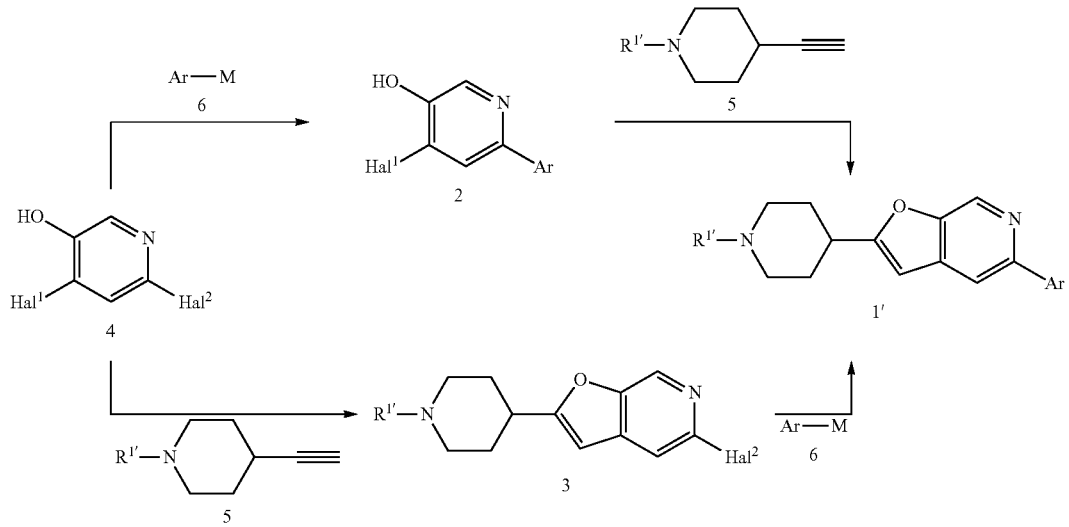

$R^{1'}$ = —$CO_2$—$R^1$, or protective group, e.g., —$CO_2{}^tBu$
$Hal^1$, $Hal^2$ = halogen or pseudohalogen, e.g., Cl, Br, I, $OSO_2CF_3$, $OSO_2Me$, $OSO_2$aryl
M = metal residue, e.g., $B(OH)_2$, $BF_3K$, $B(OCMe_2CMe_2O)$, ZnCl/Br/I, MgCl/Br/I Scheme 3 shows another way of synthesis to compounds of the invention; $R^1$, $L^Q$ and Ar have the meanings as defined hereinbefore and hereinafter. The sequence commences with addition of a carbon nucleophile or hydride to ketone 12 to obtain alcohol 13. The reduction, addition of hydride, is preferably conducted with a complex metal hydride, such as sodium borohydride, lithium borohydride, lithium triethylborohydride, diisobutylaluminum hydride, or lithium aluminum hydride. Sodium borohydride is usually used in aqueous or alcoholic solutions at −20 to 100° C., while the other reagents are preferably employed in dichloromethane, 1,2-dichloroethane, hexanes, ether, 1,4-dioxane, tetrahydrofuran, N-methylpyrrolidone, benzene, toluene, or mixtures thereof, at −80 to 60° C. The reduction may also be conducted in a stereoselective fashion to access only one enantiomer using, e.g., the conditions of the Corey-Bakshi-Shibata (CBS) reduction. The addition of a carbon nucleophile may be achieved with alkyl metal compounds, wherein the metal is a positively charged group including a metal such as Li, Mg, Ce, Zn, and/or In. The addition with a Li, Mg, or Ce compound is preferably carried out in tetrahydrofuran, ether, 1,4-dioxane, toluene, hexanes, or mixtures thereof at low temperature, −80 to 10° C. Zn and In carbanions are less reactive and usually need higher temperature, −20 to 80° C., to be added. Certain species of the latter carbanions may be employed in aqueous or alcoholic solutions.

Intramolecular substitution of the leaving group LG with oxygen provides target compound I''. For LG equals F, $SO_2C_{1-4}$-alkyl, $SO_2$-aryl, or $NO_2$, the reaction is preferably carried out in the presence of a base, such as NaH, $CaH_2$, BuLi, $KO^tBu$, or KOH, in toluene, tetrahydrofuran, 1,4-dioxane, N,N-dimethylformamide, N,N-dimethylacetamide, N-methylpyrrolidone, or mixtures thereof, at 20 to 200° C. For LG is Cl, Br, or I, the reaction is preferably conducted in the presence of a transition metal catalyst, such as Pd or Cu species.

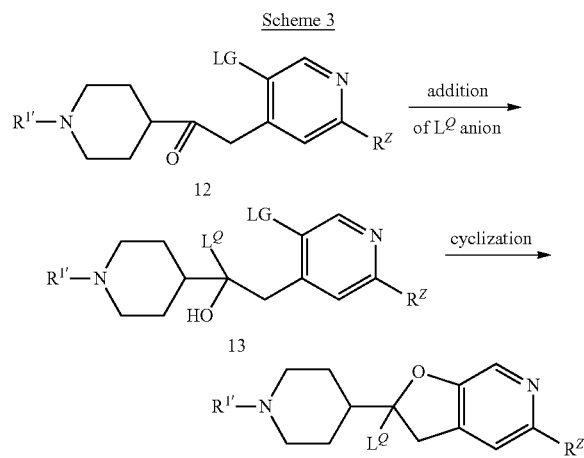

Scheme 3

$R^{1'} = \text{—}CO_2\text{—}R^1$ or protective group, e.g., $\text{—}CO_2^tBu$
LG = leaving group, e.g., F, Cl, Br, I, $OSO_2C_{1-4}$-alkyl, $SO_2$aryl, $NO_2$
$R^Z$ = Ar or group that allows introduction of Ar, e.g., as described above The dihydrofuran ring may also be formed from compound 13', bearing an additional hydroxy group on the aromatic ring. Intramolecular substitution of the aliphatic OH group with the heteroaromatic O group may be accomplished using a phosphine and an azodicarboxylic ester or amide in tetrahydrofuran, 1,4-dioxane, diethyl ether, toluene, benzene, dichloromethane, or mixtures thereof at −30 to 100° C. (Mitsunobu reaction). Triphenylphosphine or tributylphosphine combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide are common combinations for this transformation. Alternatively, the aliphatic OH group may be transformed into a leaving group, such as Cl, Br, I, $OSO_2CH_3$, and $OSO_2Ph$, and then displaced with the aromatic O under basic conditions. Suited bases may be, for instance, carbonates, e.g. $Cs_2CO_3$ and $K_2CO_3$, hydrides, e.g. NaH, alcoholates, e.g. NaOMe and $KO^tBu$, hydroxides, e.g. KOH and NaOH, that are preferably employed in toluene, tetrahydrofuran, N,N-dimethylformamide, N,N-dimethylacetamide, N-methylpyrrolidinone, dimethyl sulfoxide, alcohol, water, and mixtures thereof. The reaction may be carried out such that the aliphatic hydroxy group is substituted with complete inversion of configuration delivering an enantiomerically enriched or pure product provided that an enantiomerically enriched or pure starting compound is used.

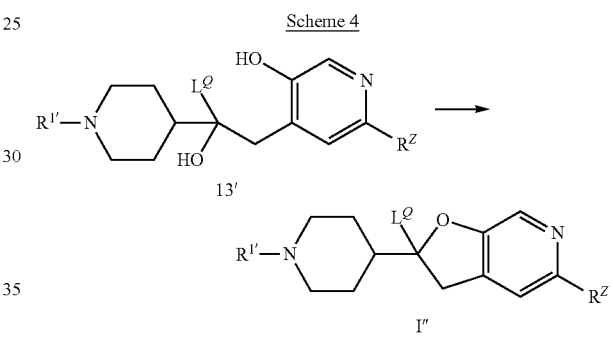

Scheme 4

$R^{1'} = \text{—}CO_2\text{—}R^1$ or protective group, e.g., $\text{—}CO_2^tBu$
$R^Z$ = Ar or group that allows introduction of Ar, e.g., as described above Intermediate 12 may be accessed as delineated in Scheme 5; $R^1$ and Ar have the meanings as defined hereinbefore and hereinafter. A carboxylic acid derivative 14 can be merged with an aromatic compound 15, that bears an anionic carbon center attached to the aromatic ring, to provide intermediate 12' (route a.). Suited carboxylic acid derivatives may be e.g. carboxylic halides, carboxylic esters, carboxylic anhydrides, and carboxylic amides, while preferred nucleophile precursors 15 are derived from EWG=H. The reaction is mediated by a base that deprotonates compound 15 to generate the anion which, in turn, adds to the carboxylic function of 14 to give 12'. Most preferred bases are selected from amides, e.g. $LiN(SiMe_3)_2$ and $LiN^iPr_2$, that may be used in solvents such as toluene, tetrahydrofuran, 1,4-dioxane, N,N-dimethylformamide, N,N-dimethylacetamide, N-methylpyrrolidinone, dimethyl sulfoxide, or mixtures thereof. For compounds 12' bearing for EWG a group other than H milder bases may be used. The EWG group in these cases may be removed afterwards by hydrolysis followed by decarboxylation, suitable for EWG=ester or cyano, or reduction, suitable for EWG=nitro or sulfonyl.

Combination of compounds 16 and 17 is another way of synthesis for intermediate 12 (route b.). Depending on the reactivity of the coupling partners, the reaction is best conducted in the presence of a transition metal catalyst or without an additive. For example, compound 16 bearing a boronic acid (M=B(OH)$_2$) and compound 17 having a carboxylic chloride (X=Cl) may be coupled using a Pd catalyst, e.g. Pd(PPh$_3$)$_4$, and a base, e.g. K$_3$PO$_4$, in a solvent, e.g. toluene or 1,4-doxane, at 60 to 120° C. A compound 16 with M=Li or MgCl may be matched with an electrophile 17 bearing a carboxamide group (X=N(OMe)Me). The reaction is commonly conducted in tetrahydrofuran, 1,4-dioxane, ether, toluene, or mixtures thereof, at −70 to 40° C., optionally in the presence of an additive such as CeCl$_3$. Compound 12″ may be converted to intermediate 12 by reduction of the double bond with hydrogen or a formate in the presence of a transition metal, e.g. Pd on carbon, or a hydride, e.g. [CuH(PPh$_3$)]$_6$.

Scheme 5 a.

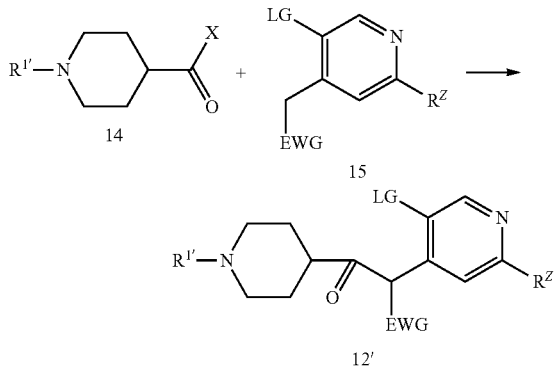

b.

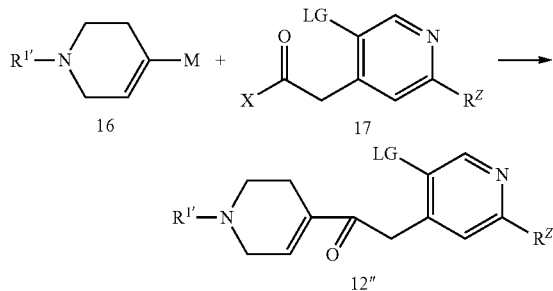

R$^{1'}$ = R$^1$ or protective group, e.g., —CO$_2$$^t$Bu
R$^Z$ = Ar or group that allows introduction of Ar, e.g., as described above
EWG = H or electron withdrawing group, e.g., CO$_2$C$_{1-4}$-alkyl, CN, SO$_2$C$_{1-4}$-alkyl, NO$_2$
LG = leaving group, e.g., F, Cl, Br, I, SO$_2$C$_{1-4}$-alkyl, SO$_2$-aryl, NO$_2$
M = metal residue, e.g., B(OH)$_2$, BF$_3$K, B(OCMe$_2$CMe$_2$O), ZnCl/Br/I, MgCl/Br/I, CeCl$_2$
X = leaving group, e.g., Cl, OC$_{1-4}$-alkyl, N(OMe)Me The synthetic routes presented may rely on the use of protecting groups.

For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the activation of the G-protein-coupled receptor GPR119 with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk (*) may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

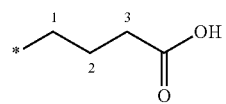

wherein the carboxy group is attached to the third carbon atom of the propyl group. The terms "1-methylpropyl-", "2,2-dimethylpropyl-" or "cyclopropylmethyl-" group represent the following groups:

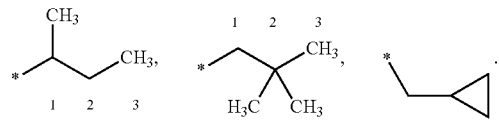

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$, Many of the terms given above may be used repeatedly in the definition of a formula or group and in each case have one of the meanings given above, independently of one another.

Pharmacological Activity

The activity of the compounds of the invention may be demonstrated using the following assay:

The compounds of the invention modulate the activity of the G-protein-coupled receptor GPR119. The effect of the compounds on the activation of GPR119 and on the stimulation of intracellular cAMP concentration is determined using the AlphaScreen cAMP Assay Kit (Cat.No.#6760625R) made by Perkin Elmer.

MIN6 cells [Miyazaki J et al., Endocrinology. 1990 July; 127(1):126-32] are stably transfected with an expression vector for human GPR119 cDNA (Acc. No. NP_848566). Min-6/hGPR119 cells are cultured in DMEM, 10% FBS, 50 µM β-mercaptoethanol, 0.3 mg/mL Geniticin, 2 mM GlutaMAX at 37° C., 5% $CO_2$. For the assay, the cells are seeded in Optiplates (white, 384-well, 160W-barcoded, TC, sterile with lid, Cat.No.#6007688 (Perkin Elmer); 10000 cells/well; 50 µL). The plates covered with lids are then incubated for 24 hours at 37° C., 5% $CO_2$. After the medium is aspirated from the wells completely, 10 µl of the test compound are added, the compounds are diluted using stimulating buffer (140 mM NaCl, 3.6 mM KCl, 0.5 mM $NaH_2PO_4$, 0.5 mM $MgSO_4$, 1.5 mM $CaCl_2$, 10 mM Hepes, 5 mM $NaHCO_3$; pH 7.4. 0.5 mM IBMX and 0.1% BSA, the final DMSO concentration is 1%). After 45 minutes incubation at room temperature (approx. 20° C.), the cAMP concentrations are determined using the AlphaScreen cAMP Assay Kit (Cat.No.#6760625R from PerkinElmer). 10 µl of Biotin-cAMP (final concentration 1 U/well in lysing buffer (5 mM Hepes (pH 7.4), 0.1% BSA, 0.5% Tween) and 10 µL Bead solution (final concentration 1 U/well in lysing buffer) are added. The plates are incubated for another 2 hours at room temperature. The cAMP concentrations are calculated using a cAMP standard curve from the Alpha Screen Counts. The data analysis is carried out by calculating the $EC_{50}$ value and the maximum value based on a positive control, using suitable software (Graphpad Prism). The compounds according to the invention increase the intracellular cAMP level in the range of 3-5.

The compounds according to the invention typically have $EC_{50}$ values in the range from about 1 nM to about 10 µM, preferably less than 1 µM, more preferably less than 100 nM.

$EC_{50}$ values for compounds according to the invention are shown in the following Table. The number of the compound corresponds to the number of the Example in the experimental section.

| Example | $EC_{50}$ [nM] | Example | $EC_{50}$ [nM] | Example | $EC_{50}$ [nM] |
|---|---|---|---|---|---|
| 1 | 5 | 2 | 6 | 3 | 6 |
| 4 | 5 | 5 | 109 | 6 | 7 |
| 7 | 3 | 8 | 4 | 9 | 1 |

In view of their ability to modulate the activity of the G-protein-coupled receptor GPR119, in particular an agonistic activity, the compounds of general formula (I) according to the invention, including the corresponding salts thereof, are theoretically suitable for the treatment of all those diseases or conditions which may be affected or which are mediated by the activation of the G-protein-coupled receptor GPR119.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR119 in a patient, preferably in a human.

In yet another aspect the present invention relates to a method for treating a disease or condition mediated by the activation of the G-protein-coupled receptor GPR119 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR119 embrace metabolic diseases or conditions.

According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macro-angiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid) receptor, MCH-1 receptor antagonists, MC4 receptor agonists, NPY5 or NPY2 antagonists, 33-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR119, in particular diseases or conditions as described hereinbefore and hereinafter.

In yet another aspect the present invention relates a method for treating a disease or condition mediated by the activation of the G-protein-coupled receptor GPR119 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times. The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

EXAMPLES

The Examples that follow are intended to illustrate the present invention without restricting it. The term "room temperature" designates a temperature of about 20° C.

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

Parameters of analytical HPLC employed for characterization of products (TFA denotes trifluoroacetic acid):

| Method: | 1 |
| --- | --- |
| Device: | Agilent 1200 with DA and MS detector |
| Column: | Sunfire C18 3.0 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [ml/min] | Temperature [° C.] |
| --- | --- | --- | --- | --- |
| 0.0 | 97 | 3 | 2.2 | 60 |
| 0.2 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

| Method: | 2 |
| --- | --- |
| Device: | Agilent 1200 with DA and MS detector |
| Column: | XBridge C18 3.0 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [ml/min] | Temperature [° C.] |
| --- | --- | --- | --- | --- |
| 0.0 | 97 | 3 | 2.2 | 60 |
| 0.2 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

| Method: | 3 |
| --- | --- |
| Device: | Agilent 1100 with DA and MS detector |
| Column: | XBridge C18, 4, 6 × 30 mm, 3.5 μm |
| Column Supplier: | Waters |

| Gradient/ Solvent Time [min] | % Sol [H$_2$O, 0.1% HCO$_2$H] | % Solvent [Methanol] | Flow [ml/min] | Temperature [° C.] |
| --- | --- | --- | --- | --- |
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

| Method: | 4 |
| --- | --- |
| Device: | Agilent 1200 with DA and MS detector |
| Column: | XBridge C18 3.0 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [ml/min] | Temperature [° C.] |
| --- | --- | --- | --- | --- |
| 0.0 | 97 | 3 | 2.2 | 60 |
| 0.2 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

Intermediate 1

4-[2-(5-Bromo-2-chloro-pyridin-4-yl)-acetyl]-piperidine-1-carboxylic acid tert-butyl ester

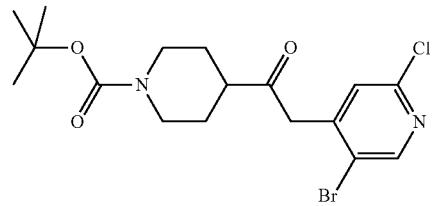 [SMILES: CC(C)(C)OC(=O)N1CCC(C(=O)Cc2cc(Cl)ncc2Br)CC1]

Lithium bis(trimethylsilyl)amide (1.0 mol/L in tetrahydrofuran; 11.00 mL) is added dropwise to 5-bromo-2-chloro-4-picoline (0.95 g) dissolved in tetrahydrofuran (15 mL) at −40° C. under argon atmosphere. The mixture is stirred for 2 h at −35 to −45° C. prior to addition of piperidine-1,4-dicarboxylic acid 1-tert-butyl ester 4-ethyl ester (1.33 g) dissolved in tetrahydrofuran (15 mL). The reaction mixture is allowed to warm to room temperature over a period of 1 h. Ice-cold water is added and the mixture is extracted with ethyl acetate. The combined extracts are washed with brine, dried (MgSO$_4$), and concentrated. The residue is chromatographed on silica gel (cyclohexane/ethyl acetate 75:25→60:40) to give the title compound. Mass spectrum (ESI$^+$): m/z=417/419/421 (Cl+Br) [M+H]$^+$.

Intermediate 2

4-[2-(5-Bromo-2-chloro-pyridin-4-yl)-1-hydroxy-ethyl]-piperidine-1-carboxylic acid tert-butyl ester

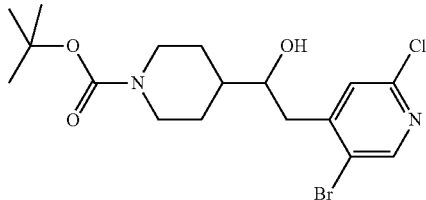 [SMILES: CC(C)(C)OC(=O)N1CCC(C(O)Cc2cc(Cl)ncc2Br)CC1]

Sodium borohydride (0.24 g) is added to an ice-cold solution of 4-[2-(5-bromo-2-chloro-pyridin-4-yl)-acetyl]-piperidine-1-carboxylic acid tert-butyl ester (1.65 g) in tetrahydrofuran (40 mL) and water (10 mL). The resulting mixture is stirred for 0.5 h. 2 N aqueous citric acid solution is added and the mixture is extracted with ethyl acetate. The combined extracts are washed with aqueous NaHCO$_3$ solution and brine, dried (MgSO$_4$), and concentrated. The residue is chromatographed on silica gel (cyclohexane/ethyl acetate 65:35) to give the title compound. Mass spectrum (ESI$^+$): m/z=419/421/423 (Cl+Br) [M+H]$^+$.

Intermediate 3

4-(5-Chloro-2,3-dihydro-furo[2,3-c]pyridin-2-yl)-piperidine-1-carboxylic acid tert-butyl ester

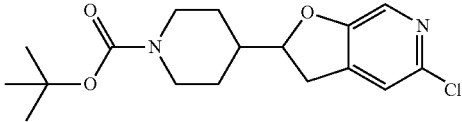 [SMILES: CC(C)(C)OC(=O)N1CCC(C2Cc3cc(Cl)ncc3O2)CC1]

A mixture of 4-[2-(5-bromo-2-chloro-pyridin-4-yl)-1-hydroxy-ethyl]-piperidine-1-carboxylic acid tert-butyl ester (11.60 g), palladium acetate (0.50 g), racemic 2-(di-tert-butylphosphino)-1,1'-binapthyl (1.00 g), cesium carbonate (14.00 g), and toluene (150 mL) is stirred at 110° C. under argon atmosphere for 5 h. After cooling to room temperature, ethyl acetate and water are added. The organic phase is separated, washed with brine, dried (MgSO$_4$), and concentrated. The residue is chromatographed on silica gel (cyclohexane/ethyl acetate 70:30→50:50) to give the title compound. Mass spectrum (ESI$^+$): m/z=339/341 (Cl) [M+H]$^+$.

Intermediates 4 and 5

(R)-4-(5-Chloro-2,3-dihydro-furo[2,3-c]pyridin-2-yl)-piperidine-1-carboxylic acid tert-butyl ester and (S)-4-(5-Chloro-2,3-dihydro-furo[2,3-c]pyridin-2-yl)-piperidine-1-carboxylic acid tert-butyl ester Intermediate 4

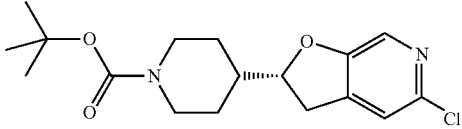

Intermediate 5

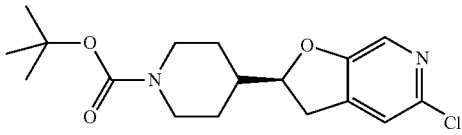

The title compounds are obtained in separate fractions upon SFC on chiral phase of racemic Intermediate 3 (column: Daicel IC, 250×20 mm; mobile phase: ethanol containing 0.2% diethylamine/sc carbon dioxide 25:75; flow rate 50 ml/min). The configurations of the stereocenters of Intermediates 4 and 5 were unambiguously determined by X-ray analysis of a crystal structure of Intermediate 5; retention times on the SFC on chiral phase (Daicel IC, 250×4.6 mm; mobile phase: ethanol containing 0.2% diethylamine/sc carbon dioxide 25:75; flow rate 4 ml/min): Intermediate 4: $t_R$=1.64 min; Intermediate 5; $t_R$=1.91 min.

Intermediate 6

(R)-4-[5-(1-Methanesulfonyl-1,2,3,6-tetrahydro-pyridin-4-yl)-2,3-dihydro-furo[2,3-c]pyridin-2-yl]-piperidine-1-carboxylic acid tert-butyl ester

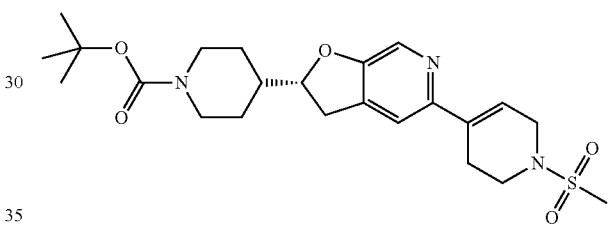

A mixture of (R)-4-(5-chloro-2,3-dihydro-furo[2,3-c]pyridin-2-yl)-piperidine-1-carboxylic acid tert-butyl ester (0.40 g), 1-methanesulfonyl-4-(4,4,5,5-tetramethyl-[1,3,2]dioxaborolan-2-yl)-1,2,3,6-tetrahydro-pyridine (0.38 g), 2 M aqueous Na$_2$CO$_3$ solution (1.3 mL), and 1,4-dioxane (8 mL) is sparged with argon for 5 min. Tetrakis(triphenylphosphine)palladium(0) (0.10 g) is added and the mixture is stirred in a microwave oven at 170° C. for 1 h. After cooling to room temperature, water is added and the resulting mixture is extracted with ethyl acetate. The combined extract is washed with brine, dried (Na$_2$SO$_4$), and concentrated. The residue is chromatographed on silica gel (cyclohexane/ethyl acetate 3:7→0:1) to give the title compound. Mass spectrum (ESI$^+$): m/z=464 [M+H]$^+$.

Intermediate 7

(R)-5-(1-Methanesulfonyl-1,2,3,6-tetrahydro-pyridin-4-yl)-2-piperidin-4-yl-2,3-dihydro-furo[2,3-c]pyridine

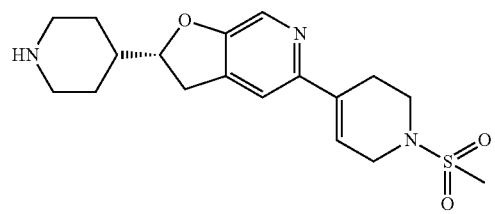 [SMILES: CS(=O)(=O)N1CC=C(c2cc3c(cn2)O[C@@H](C2CCNCC2)C3)CC1]

Trifluoroacetic acid (2 mL) is added to a solution of (R)-4-[5-(1-methanesulfonyl-1,2,3,6-tetrahydro-pyridin-4-yl)-2,3-dihydro-furo[2,3-c]pyridin-2-yl]-piperidine-1-carboxylic acid tert-butyl ester (1.0 g) in dichloromethane (10 mL) at room temperature. The solution is stirred at room temperature overnight and then diluted with dichloromethane, 2 N aqueous NaOH solution, and saturated aqueous Na$_2$CO$_3$ solution. The resulting mixture is vigorously stirred for 20 min and then extracted with dichloromethane. The combined extract is dried (Na$_2$SO$_4$) and concentrated to give the title compound. Mass spectrum (ESI$^+$): m/z=364 [M+H]$^+$.

Intermediate 8

(R)-4-[5-(4-Methanesulfonyl-phenyl)-2,3-dihydro-furo[2,3-c]pyridin-2-yl]-piperidine-1-carboxylic acid tert-butyl ester

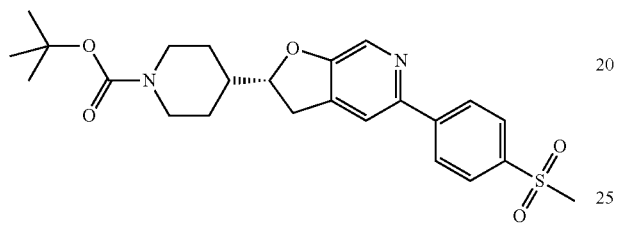

The title compound is prepared from (R)-4-(5-chloro-2,3-dihydro-furo[2,3-c]pyridin-2-yl)-piperidine-1-carboxylic acid tert-butyl ester and 4-(methylsulfonyl)-phenylboronic acid following a procedure analogous to that described for Intermediate 6. Mass spectrum (ESI$^+$): m/z=459 [M+H]$^+$.

Intermediate 9

(R)-5-(4-Methanesulfonyl-phenyl)-2-piperidin-4-yl-2,3-dihydro-furo[2,3-c]pyridine

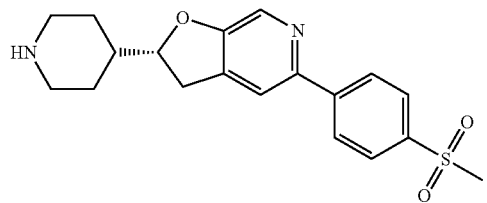 [SMILES: CS(=O)(=O)c1ccc(-c2cc3c(cn2)O[C@@H](C2CCNCC2)C3)cc1]

The title compound is prepared from (R)-4-[5-(4-methanesulfonyl-phenyl)-2,3-dihydro-furo[2,3-c]pyridin-2-yl]-piperidine-1-carboxylic acid tert-butyl ester following a procedure analogous to that described for Intermediate 7. Mass spectrum (ESI$^+$): m/z=359 [M+H]$^+$.

Intermediate 10

4-[2-(5-Bromo-2-chloro-pyridin-4-yl)-1-hydroxy-1-methyl-ethyl]-piperidine-1-carboxylic acid tert-butyl ester

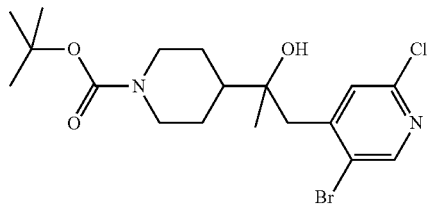 [SMILES: CC(C)(C)OC(=O)N1CCC(C(C)(O)Cc2cc(Cl)ncc2Br)CC1]

A solution of 4-[2-(5-bromo-2-chloro-pyridin-4-yl)-acetyl]-piperidine-1-carboxylic acid tert-butyl ester (9.80 g) in tetrahydrofuran (6 mL) is added dropwise to an ice-cold solution of methyl magnesium bromide (1.4 mol/L in toluene/tetrahydrofuran 75:25; 74.0 mL). The reaction mixture is stirred for 30 min before the cooling bath is removed. After stirring the mixture at room temperature for 1 h, the mixture is poured into aqueous NH$_4$Cl solution. The resulting mixture is extracted with ethyl acetate, and the combined extracts are dried (MgSO$_4$) and concentrated. The residue containing significant amounts of starting material is azeotropically dried using toluene and resubmitted to the reaction conditions and work-up procedure described. The crude product is purified by preparative HPLC (column: Waters X-Bridge C18; mobile phase: water+0.125% NH$_4$OH/methanol 90:10→100:0) to give the title compound. Mass spectrum (ESI$^+$): m/z=433/435/437 (Cl+Br) [M+H]$^+$.

Intermediate 11

4-(5-Chloro-2-methyl-2,3-dihydro-furo[2,3-c]pyridin-2-yl)-piperidine-1-carboxylic acid tert-butyl ester

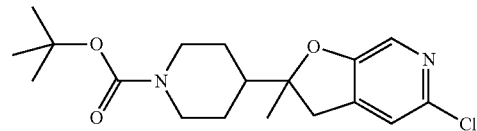 [SMILES: CC(C)(C)OC(=O)N1CCC(C2(C)Cc3cc(Cl)ncc3O2)CC1]

The title compound is prepared from 4-[2-(5-bromo-2-chloro-pyridin-4-yl)-1-hydroxy-1-methyl-ethyl]-piperidine-1-carboxylic acid tert-butyl ester following a procedure analogous to that described for Intermediate 3. Mass spectrum (ESI$^+$): m/z=353/355 (Cl) [M+H]$^+$.

Intermediates 12 and 13

(R)-4-(5-Chloro-2-methyl-2,3-dihydro-furo[2,3-c]pyridin-2-yl)-piperidine-1-carboxylic acid tert-butyl ester and (S)-4-(5-Chloro-2-methyl-2,3-dihydro-furo[2,3-c]pyridin-2-yl)-piperidine-1-carboxylic acid tert-butyl ester Intermediate 12

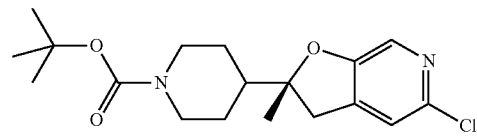

Intermediate 13

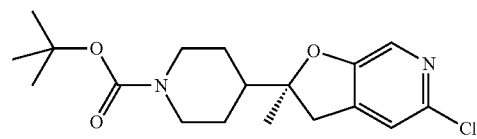

The title compounds are obtained in separate fractions upon SFC on chiral phase of racemic Intermediate 11 (column: Daicel IC, 250×20 mm; mobile phase: methanol containing 0.2% diethylamine/sc carbon dioxide 25:75; flow rate 60 ml/min). The configurations of the stereocenters of Intermediates 12 and 13 were unambiguously determined by X-ray analysis of the crystal structure of a derivative of Intermediate 13, (S)-2-[1-(4-bromo-benzenesulfonyl)-piperidin-4-yl]-5-chloro-2,3-dihydro-furo[2,3-c]pyridine (obtained upon acid induced liberation of the piperidine N of Intermediate 13 and its subsequent sulfonylation with 4-bromo-benzenesulfonyl chloride); retention times on the SFC on chiral phase (Daicel IC, 250×4.6 mm; mobile phase: methanol containing 0.2% diethylamine/sc carbon dioxide 25:75; flow rate 4 ml/min):

Intermediate 12: $t_R$=3.77 min; Intermediate 13: $t_R$=4.42 min.

Intermediate 14

(R)-4-[5-(4-Methanesulfonyl-phenyl)-2-methyl-2,3-dihydro-furo[2,3-c]pyridin-2-yl]-piperidine-1-carboxylic acid tert-butyl ester

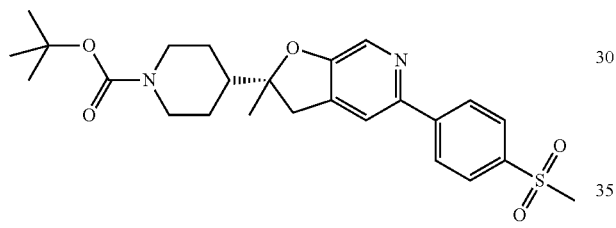

The title compound is prepared from (R)-4-(5-chloro-2-methyl-2,3-dihydro-furo[2,3-c]pyridin-2-yl)-piperidine-1-carboxylic acid tert-butyl ester and 4-(methanesulfonyl)-phenylboronic acid following a procedure analogous to that described for Intermediate 6. Mass spectrum (ESI+): m/z=473 [M+H]+.

Intermediate 15

(R)-5-(4-Methanesulfonyl-phenyl)-2-methyl-2-piperidin-4-yl-2,3-dihydro-furo[2,3-c]pyridine

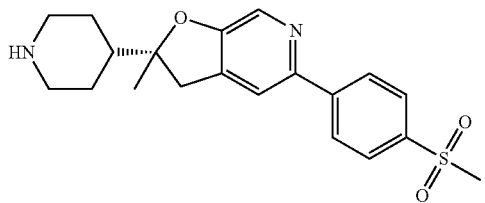 [SMILES: C[C@]1(C2CCNCC2)Cc2cc(-c3ccc(S(C)(=O)=O)cc3)ncc2O1]

The title compound is prepared from (R)-4-[5-(4-methanesulfonyl-phenyl)-2-methyl-2,3-dihydro-furo[2,3-c]pyridin-2-yl]-piperidine-1-carboxylic acid tert-butyl ester following a procedure analogous to that described for Intermediate 7. Mass spectrum (ESI+): m/z=373 [M+H]+.

Intermediate 16

(S)-4-[5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid tert-butyl ester

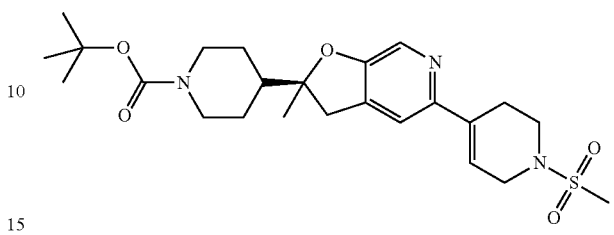

The title compound is prepared from (S)-4-(5-chloro-2-methyl-2,3-dihydro-furo[2,3-c]pyridin-2-yl)-piperidine-1-carboxylic acid tert-butyl ester and 1-(methylsulfonyl)-4-(4,4,5,5-tetramethyl-1,3,2-dioxaborolan-2-yl)-1,2,3,6-tetrahydropyridine following a procedure analogous to that described for Intermediate 6. Mass spectrum (ESI+): m/z=478 [M+H]+.

Intermediate 17

(S)-5-(1-Methanesulfonyl-1,2,3,6-tetrahydro-pyridin-4-yl)-2-methyl-2-piperidin-4-yl-2,3-dihydro-furo[2,3-c]pyridine

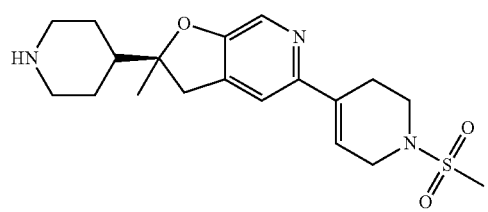 [SMILES: C[C@@]1(C2CCNCC2)Cc2cc(C3=CCN(S(C)(=O)=O)CC3)ncc2O1]

The title compound is prepared from (S)-4-[5-(1-methanesulfonyl-1,2,3,6-tetrahydro-pyridin-4-yl)-2-methyl-2,3-dihydro-furo[2,3-c]pyridin-2-yl]-piperidine-1-carboxylic acid tert-butyl ester following a procedure analogous to that described for Intermediate 7. Mass spectrum (ESI+): m/z=378 [M+H]+.

Intermediate 18

(R)-4-[5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid tert-butyl ester

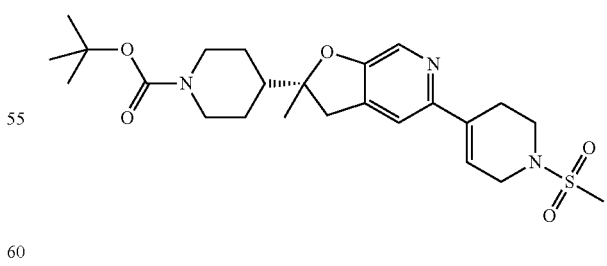

The title compound is prepared from (R)-4-(5-chloro-2-methyl-2,3-dihydro-furo[2,3-c]pyridin-2-yl)-piperidine-1-carboxylic acid tert-butyl ester and 1-(methylsulfonyl)-4-(4,4,5,5-tetramethyl-1,3,2-dioxaborolan-2-yl)-1,2,3,6-tetrahydropyridine following a procedure analogous to that described for Intermediate 6. Mass spectrum (ESI+): m/z=478 [M+H]+.

Intermediate 19

(R)-5-(1-Methanesulfonyl-1,2,3,6-tetrahydro-pyridin-4-yl)-2-methyl-2-piperidin-4-yl-2,3-dihydro-furo[2,3-c]pyridine

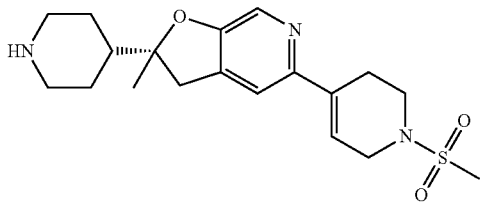 [SMILES: C[C@]1(C2CCNCC2)Cc2cc(C3=CCN(S(C)(=O)=O)CC3)ncc2O1]

The title compound is prepared from (R)-4-[5-(1-methanesulfonyl-1,2,3,6-tetrahydro-pyridin-4-yl)-2-methyl-2,3-dihydro-furo[2,3-c]pyridin-2-yl]-piperidine-1-carboxylic acid tert-butyl ester following a procedure analogous to that described for Intermediate 7. Mass spectrum (ESI$^+$): m/z=378 [M+H]$^+$.

Intermediate 20

Carbonic acid 4-nitro-phenyl ester (S)-2,2,2-trifluoro-1-methyl-ethyl ester

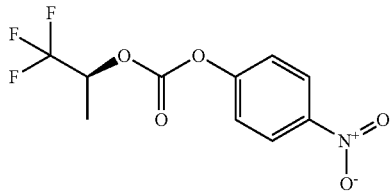 [SMILES: C[C@H](OC(=O)Oc1ccc([N+](=O)[O-])cc1)C(F)(F)F]

Triethylamine (2.3 mL) is added to a solution of 4-dimethylaminopyridine (13 mg), (S)-1,1,1-trifluoro-propan-2-ol (75% in tert-butyl methyl ether; 2.00 g), and 4-nitrophenyl chloroformate (2.90 g) in dichloromethane (80 mL) chilled in an ice bath. The solution is stirred in the cooling bath for 30 min and then at room temperature overnight. The solution is washed with 10% aqueous K$_2$CO$_3$ solution and water and dried (MgSO$_4$). The solvent is evaporated and the residue is chromatographed on silica gel (dichloromethane) to give the title compound.

Intermediate 21

Carbonic acid 4-nitro-phenyl ester (R)-2,2,2-trifluoro-1-methyl-ethyl ester

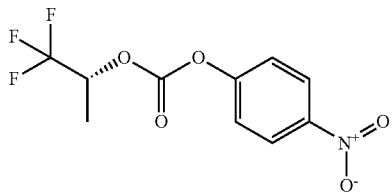 [SMILES: C[C@@H](OC(=O)Oc1ccc([N+](=O)[O-])cc1)C(F)(F)F]

The title compound is prepared from (R)-1,1,1-trifluoropropan-2-ol and 4-nitrophenyl chloroformate following a procedure analogous to that described for Intermediate 20.

Example 1

(S)-4-[(R)-5-(4-Methanesulfonyl-phenyl)-2,3-dihydro-furo[2,3-c]pyridin-2-yl]-piperidine-1-carboxylic acid 2,2,2-trifluoro-1-methyl-ethyl ester

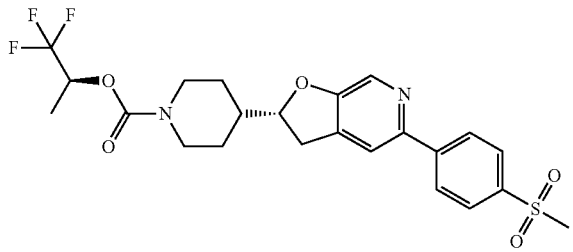 [SMILES: C[C@H](OC(=O)N1CCC([C@H]2Cc3cc(-c4ccc(S(C)(=O)=O)cc4)ncc3O2)CC1)C(F)(F)F]

Carbonic acid 4-nitro-phenyl ester (S)-2,2,2-trifluoro-1-methyl-ethyl ester (85 mg) is added to a solution of (R)-5-(4-methanesulfonyl-phenyl)-2-piperidin-4-yl-2,3-dihydro-furo[2,3-c]pyridine (100 mg) and N,N-diisopropyl-ethylamine (60 μL) in tetrahydrofuran (2 mL) at room temperature. The solution is stirred at room temperature overnight and then washed with 1 N aqueous NaOH solution (3×), water, and brine. The organic phase is dried (MgSO$_4$) and concentrated. The residue is chromatographed on silica gel (cyclohexane/ethyl acetate 1:1→1:3) to give the title compound. LC (method 1): t$_R$=1.00 min; Mass spectrum (ESI$^+$): m/z=499 [M+H]$^+$.

Example 2

(R)-4-[(R)-5-(4-Methanesulfonyl-phenyl)-2,3-dihydro-furo[2,3-c]pyridin-2-yl]-piperidine-1-carboxylic acid 2,2,2-trifluoro-1-methyl-ethyl ester

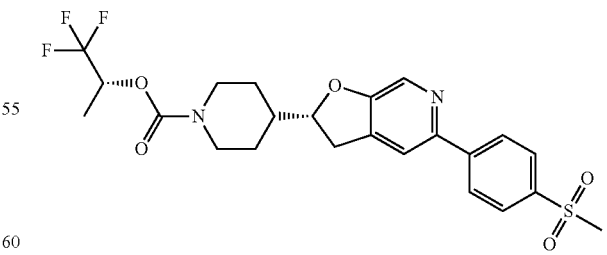

The title compound is prepared from (R)-5-(4-methanesulfonyl-phenyl)-2-piperidin-4-yl-2,3-dihydro-furo[2,3-c]pyridine and carbonic acid 4-nitro-phenyl ester (R)-2,2,2-trifluoro-1-methyl-ethyl ester following a procedure analogous to that described for Example 1. LC (method 2): $t_R$=1.07 min; Mass spectrum (ESI⁺): m/z=499 [M+H]⁺.

Example 3

(R)-4-[(R)-5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester

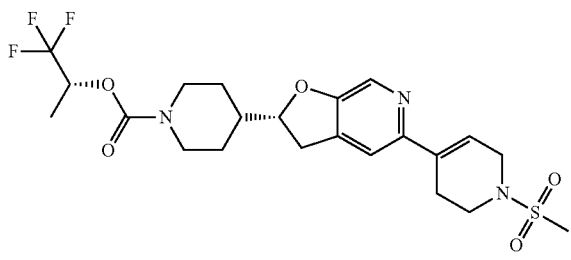 [SMILES: C[C@@H](OC(=O)N1CCC([C@H]2Cc3cc(C4=CCN(S(C)(=O)=O)CC4)ncc3O2)CC1)C(F)(F)F]

The title compound is prepared from (R)-5-(1-methanesulfonyl-1,2,3,6-tetrahydro-pyridin-4-yl)-2-piperidin-4-yl-2,3-dihydro-furo[2,3-c]pyridine and carbonic acid 4-nitro-phenyl ester (R)-2,2,2-trifluoro-1-methyl-ethyl ester following a procedure analogous to that described for Example 1. LC (method 2): $t_R$=0.97 min; Mass spectrum (ESI⁺): m/z=504 [M+H]⁺.

Example 4

(S)-4-[(R)-5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester

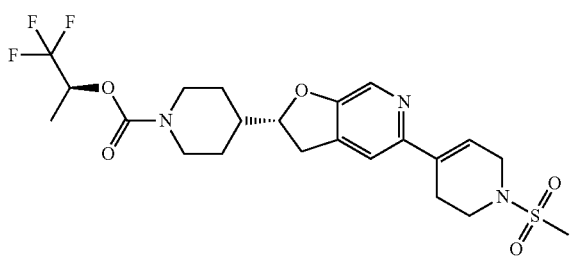 [SMILES: C[C@H](OC(=O)N1CCC([C@H]2Cc3cc(C4=CCN(S(C)(=O)=O)CC4)ncc3O2)CC1)C(F)(F)F]

The title compound is prepared from (R)-5-(1-methanesulfonyl-1,2,3,6-tetrahydro-pyridin-4-yl)-2-piperidin-4-yl-2,3-dihydro-furo[2,3-c]pyridine and carbonic acid 4-nitro-phenyl ester (S)-2,2,2-trifluoro-1-methyl-ethyl ester following a procedure analogous to that described for Example 1. LC (method 1): $t_R$=0.86 min; Mass spectrum (ESI⁺): m/z=504 [M+H]⁺.

Example 5

(S)-4-[(S)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester

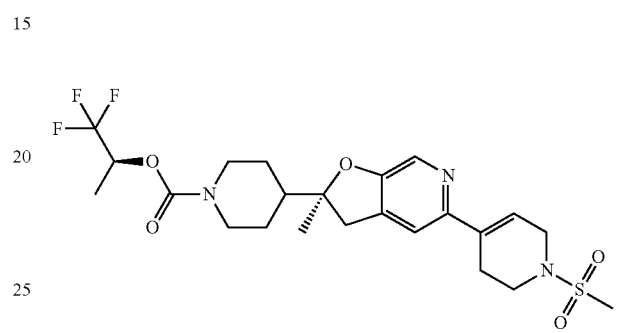

The title compound is prepared from (S)-5-(1-methanesulfonyl-1,2,3,6-tetrahydro-pyridin-4-yl)-2-methyl-2-piperidin-4-yl-2,3-dihydro-furo[2,3-c]pyridine and carbonic acid 4-nitro-phenyl ester (S)-2,2,2-trifluoro-1-methyl-ethyl ester following a procedure analogous to that described in Example 1. LC (method 3): $t_R$=1.54 min; Mass spectrum (ESI⁺): m/z=518 [M+H]⁺.

Example 6

(R)-4-[(R)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester

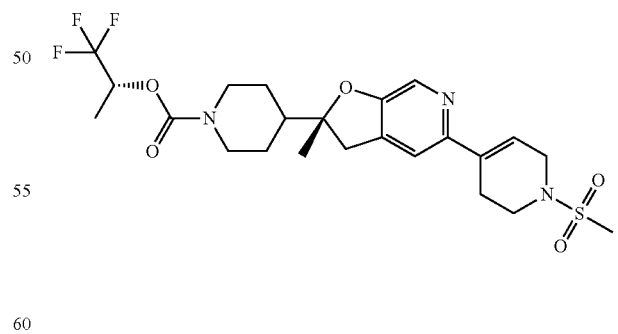

The title compound is prepared from (R)-5-(1-methanesulfonyl-1,2,3,6-tetrahydro-pyridin-4-yl)-2-methyl-2-piperidin-4-yl-2,3-dihydro-furo[2,3-c]pyridine and carbonic acid 4-nitro-phenyl ester (R)-2,2,2-trifluoro-1-methyl-ethyl ester following a procedure analogous to that described for Example 1. LC (method 4): $t_R$=0.92 min; Mass spectrum (ESI⁺): m/z=518 [M+H]⁺.

Example 7

(S)-4-[(R)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester

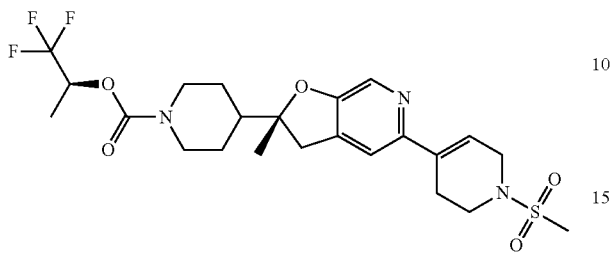

The title compound is prepared from (R)-5-(1-methanesulfonyl-1,2,3,6-tetrahydro-pyridin-4-yl)-2-methyl-2-piperidin-4-yl-2,3-dihydro-furo[2,3-c]pyridine and carbonic acid 4-nitro-phenyl ester (S)-2,2,2-trifluoro-1-methyl-ethyl ester following a procedure analogous to that described in Example 1. LC (method 2): $t_R$=0.92 min; Mass spectrum (ESI$^+$): m/z=518 [M+H]$^+$.

Example 8

(R)-4-[(R)-5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester

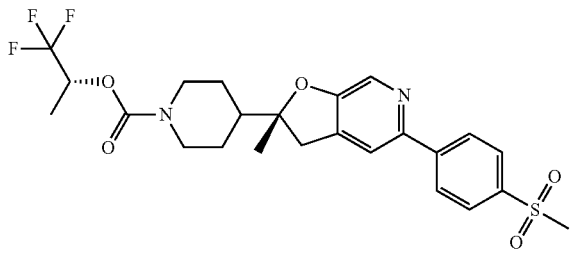 [SMILES: C[C@@H](OC(=O)N1CCC([C@@]2(C)Cc3cc(-c4ccc(S(C)(=O)=O)cc4)ncc3O2)CC1)C(F)(F)F]

The title compound is prepared from (R)-5-(4-methanesulfonyl-phenyl)-2-methyl-2-piperidin-4-yl-2,3-dihydro-furo[2,3-c]pyridine and carbonic acid 4-nitro-phenyl ester (R)-2,2,2-trifluoro-1-methyl-ethyl ester following a procedure analogous to that described in Example 1. LC (method 2): $t_R$=1.00 min; Mass spectrum (ESI$^+$): m/z=513 [M+H]$^+$.

Example 9

(S)-4-[(R)-5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester

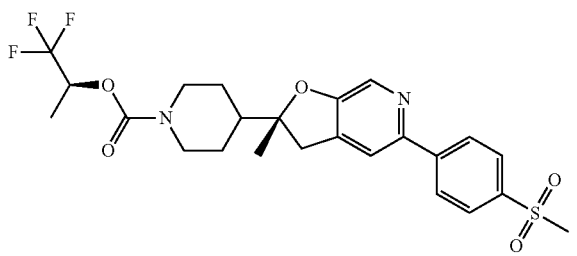 [SMILES: C[C@H](OC(=O)N1CCC([C@@]2(C)Cc3cc(-c4ccc(S(C)(=O)=O)cc4)ncc3O2)CC1)C(F)(F)F]

The title compound is prepared from (R)-5-(4-methanesulfonyl-phenyl)-2-methyl-2-piperidin-4-yl-2,3-dihydro-furo[2,3-c]pyridine and carbonic acid 4-nitro-phenyl ester (S)-2,2,2-trifluoro-1-methyl-ethyl ester following a procedure analogous to that described in Example 1. LC (method 2): $t_R$=1.01 min; Mass spectrum (ESI$^+$): m/z=513 [M+H]$^+$.

The invention claimed is:

1. A compound of formula I

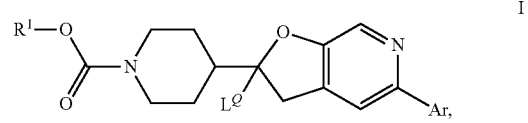

wherein:
R$^1$ is C$_{1-4}$-alkyl in which one or more hydrogen atoms are replaced by F;
Ar is

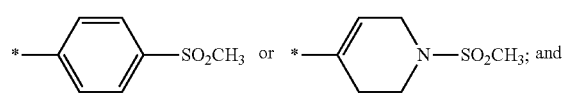 [SMILES: *c1ccc(S(C)(=O)=O)cc1 ; *C1=CCN(S(C)(=O)=O)CC1]

L$^Q$ is H or C$_{1-3}$-alkyl,
or a salt thereof.

2. The compound according to claim 1, wherein:
L$^Q$ is H or methyl,
or a salt thereof.

3. The compound according to claim 1, wherein:
R$^1$ is —CH(CH$_3$)(CF$_3$),
or a salt thereof.

4. The compound according to claim 1 selected from:
(a) 4-[5-(4-Methanesulfonyl-phenyl)-2,3-dihydro-furo[2,3-c]pyridin-2-yl]-piperidine-1-carboxylic acid 2,2,2-trifluoro-1-methyl-ethyl ester,
(b) 4-[5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester,
(c) 4-[5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester, and
(d) 4-[5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester,
or an enantiomer, diastereomer, or salt thereof.

5. The compound according to claim 4 selected from:
(1) (S)-4-[(R)-5-(4-Methanesulfonyl-phenyl)-2,3-dihydro-furo[2,3-c]pyridin-2-yl]-piperidine-1-carboxylic acid 2,2,2-trifluoro-1-methyl-ethyl ester,
(2) (R)-4-[(R)-5-(4-Methanesulfonyl-phenyl)-2,3-dihydro-furo[2,3-c]pyridin-2-yl]-piperidine-1-carboxylic acid 2,2,2-trifluoro-1-methyl-ethyl ester,
(3) (R)-4-[(R)-5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester,
(4) (S)-4-[(R)-5-(1-Methanesulfonyl-1,2,3,6-tetrahydro-pyridin-4-yl)-2,3-dihydro-furo[2,3-c]pyridin-2-yl]-piperidine-1-carboxylic acid 2,2,2-trifluoro-1-methyl-ethyl ester, (5) (S)-4-[(S)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester, (6) (R)-4-[(R)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester, (7) (S)-4-[(R)-5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid 2,2,2-trifluoro-1-methyl-ethyl ester, (8) (R)-4-[(R)-5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester, and (9) (S)-4-[(R)-5-(4-Methanesulfonyl-phenyl)-2-methyl-2,3-dihydro-furo[2,3-c]pyridin-2-yl]-piperidine-1-carboxylic acid 2,2,2-trifluoro-1-methyl-ethyl ester, or a salt thereof.

6. A pharmaceutically acceptable salt of a compound according to claim 1.

7. A pharmaceutical composition comprising a compound according to claim 1 or a pharmaceutically acceptable salt thereof, and an inert carrier or diluent.

8. A method for treating-type 2 diabetes mellitus, comprising administering to a patient in need thereof the compound according to claim 1 or a pharmaceutically acceptable salt thereof.

9. The compound according to claim 2, wherein $R^1$ is selected from a group $R^1$-G2 consisting of —$CH(CH_3)(CF_3)$, or a salt thereof.

* * * * *